(12) United States Patent
Mahler et al.

(10) Patent No.: US 8,420,027 B2
(45) Date of Patent: Apr. 16, 2013

(54) DOSING DEVICE FOR LIQUIDS

(75) Inventors: Peter H. Mahler, Kreuzwertheim (DE);
Thomas Stricker, Wertheim (DE);
Harry Siebert, Helmstadt (DE);
Eberhard Albrecht, Wertheim (DE)

(73) Assignee: Brand GmbH + Co KG, Wertheim (DE)

( * ) Notice: Subject to any disclaimer, the term of this patent is extended or adjusted under 35 U.S.C. 154(b) by 407 days.

(21) Appl. No.: 12/682,691

(22) PCT Filed: Oct. 13, 2008

(86) PCT No.: PCT/EP2008/008639
§ 371 (c)(1),
(2), (4) Date: Apr. 12, 2010

(87) PCT Pub. No.: WO2009/049842
PCT Pub. Date: Apr. 23, 2009

(65) Prior Publication Data
US 2010/0243675 A1     Sep. 30, 2010

(30) Foreign Application Priority Data
Oct. 11, 2007   (DE) .................... 20 2007 014 286 U

(51) Int. Cl.
*B01L 3/02* (2006.01)
(52) U.S. Cl.
USPC ........ 422/522; 422/501; 422/509; 73/863.31; 73/863.32; 73/864.01; 73/864.17
(58) Field of Classification Search ............... 422/501, 422/509–519, 521–522; 73/863.31–863.33, 73/864.01–864.25
See application file for complete search history.

(56) References Cited

U.S. PATENT DOCUMENTS 3,572,552 A    3/1971   Guinn
6,593,146 B1   7/2003   Lang et al.
7,470,402 B2*  12/2008  Abou Saleh et al. ......... 422/606

FOREIGN PATENT DOCUMENTS

DE    24 07 101 B1   8/1975
DE    90 03 629.8 U1  7/1990

OTHER PUBLICATIONS

International Search Report for International Application No. PCT/EP2008/008639 Dated Mar. 18, 2009.

* cited by examiner

*Primary Examiner* — Jan Ludlow
(74) *Attorney, Agent, or Firm* — Roberts Mlotkowski Safran & Cole, P.C.; David S. Safran

(57) ABSTRACT

A dosing device for liquids, with a distributor rail and a plurality of dosing units for the liquid that are hydraulically connected to the replaceable distributor rail. Each dosing unit has a valve unit, preferably a suction valve, a discharge valve and a discharge cannula. A piston-cylinder unit is detachably arranged on each valve unit for drawing in and measured discharging of the liquid. Each valve unit has a hydraulic connection element for detachable hydraulic connection to the distributor rail. The distributor rail has an elongate fluid supply line, a supply connection for the liquid being provided on an end of the distributor rail and dosing unit connections being distributed laterally along the length of the rail. Each of the dosing unit connections are detachably coupled to the hydraulic connection elements of the dosing units. The distributor rail is a replaceable part made of a preferably recyclable, injection-moldable plastic.

33 Claims, 10 Drawing Sheets

DOSING DEVICE FOR LIQUIDS

BACKGROUND OF THE INVENTION

1. Field of the Invention

The invention relates to a dosing device for liquids with a distributor rail, and a plurality of dosing units for a liquid that are hydraulically connected to the distributor rail, each dosing unit having a valve unit on which a piston-cylinder unit for drawing in and measured discharging of the liquid is detachably arranged, each valve unit having a hydraulic connection element for detachable hydraulic connection to the distributor rail.

2. Description of Relation Art

Overall, the invention relates to a dosing device for liquids as used in semi-automated or fully automated production dosing installations for filling samples or the like, particularly in the biological, chemical or pharmaceutical industry. A plurality of sample containers arranged next to one another are simultaneously filled with the desired liquid by using a multi-channel system made of a plurality of dosing units arranged next to one another.

Once a dosing cycle or a period of dosing has been completed, and when the liquid to be dosed is changed, all parts of the dosing installation exposed to the liquid have to be cleaned, possibly autoclaved or sterilized. In the case of some liquids, this is downright difficult and so there has already been a proposal for a dosing installation that is improved in terms of application and cleaning (Brochure of the Assignee of the assignee of this application, BRAND GMBH+CO KG, "Dosieranlagen und-systeme" [Dosing installations and dosing systems], 9944-93, 10/0903; WO-A-00/49418 corresponds to U.S. Pat. No. 6,593,146 B1). A dosing device for the liquid to be dosed is part of such a dosing installation. This dosing device is constantly connected to a liquid storage container or a storage line. The dosing device is equipped with electrical devices, drives and various lines required for operation.

The known dosing device, on which the invention is based, has a distributor rail and a plurality of dosing units for the liquid to be dosed that are hydraulically connected to the distributor rail. It is typical for five dosing units to be arranged on a distributor rail. Each dosing unit has a valve unit and a piston-cylinder unit detachably arranged on the valve unit. The valve unit typically has a suction valve, a discharge valve and a laterally protruding discharge cannula that can be removed from the valve unit. Each valve unit has a hydraulic connection element for detachable hydraulic connection to the distributor rail. The distributor rail itself has an elongate fluid supply line, which has at its end a supply connection for the liquid and has dosing unit connections distributed laterally along its length, arranged with equidistant spacing, which dosing unit connections are detachably coupled to the hydraulic connection elements of the dosing units.

The description of the dosing device provided above and the description of the dosing device provided below assume that, overall, the dosing device is assembled. Parts, which in principle are detachably interconnected, are interconnected. This illustrates the relationships.

Assigned to the dosing device is a motor-driven drive device, which is detachably coupled to connecting heads on the piston rods of the piston-cylinder units via a coupling device. Movement of the coupling device can lift and lower all piston rods of the adjacent piston-cylinder units in a synchronous fashion for sucking in and dosed discharge of the liquid.

In the known dosing device constituting the starting point for the teaching of the invention, the distributor rail is produced as a block of sterilizable and autoclavable metal, made in particular of aluminum or stainless steel. The fluid supply line and the dosing unit connections are formed in the block. On this distributor rail, there are also laterally spaced apart strips of hooks, which form mechanical connection elements detachably engaged with corresponding mechanical connection elements on the dosing units. Thus, on the one hand, the block-like distributor rail forms the fluid supply for the dosing units and, on the other hand, the mechanical support for the dosing units.

Measures have already been taken in the known dosing device in order to optimize it in respect of cleaning. Specifically, there, provision is made for the piston cylinder units to be designed as replaceable parts made of preferably recyclable and preferably injection-moldable plastic and to be used interchangeably. Furthermore, provision is also made for the valve units to be designed, at least to the greatest extent, as replaceable parts made of preferably recyclable and preferably injection-moldable plastic. The result of this is that it is only the complex and high-quality distributor rail that has to be cleaned and, preferably, sterilized and/or autoclaved. All add-on parts can quickly be replaced.

SUMMARY OF THE INVENTION

The object of the invention now is to improve further the known dosing device, already optimized for cleaning, in respect of the high requirements for appropriate production installations in the chemical industry and, in particular, the pharmaceutical industry.

In the case of a dosing device for liquids with the features of the preamble of claim 1, the problem highlighted above is solved by the features of the characterizing part of claim 1. Provision is made for the distributor rail also to be designed as a replaceable part made of a preferably recyclable, preferably injection-moldable plastic.

A replaceable part within the scope of the present invention is a mass-produced product from production that depends on the mold dimensions. The precise nature of the product is a result of the investment in the production tool. The replacement part itself can then be produced cost-effectively, even though it has an exact size within strict tolerances. This is optimized by virtue of the fact that a cost-effective plastic is used as a material.

It was previously assumed that the complex design of the distributor rail, which moreover also forms the mechanical spine of the dosing device, made the use of metal, in particular aluminum, very particularly stainless steel, inevitable. However, extensive trials by the applicant have shown that the distributor rail can also be designed as a replaceable part made of plastic, as can the piston-cylinder units and the valve units as well. This allows the implementation of a dosing device entirely designed as a replaceable part, the handling of which is significantly more expedient in the day-to-day use in production with the extreme requirements of the pharmaceutical industry in particular.

Cleaning can also be dispensed with in respect of the distributor rail. The risks of insufficient cleaning and rinsing or disinfectant means remaining in the distributor rail are systematically avoided. The complicated documentation relating thereto is also unnecessary. Downtimes of the corresponding installations are significantly reduced.

It was found that the distributor rail could hardly be kept sterile between sterilization and installation. According to the invention, the entire dosing device can be disposed of without being disassembled, and a replaceable dosing device made of distributor rail, valve units and piston-cylinder units can be used. This device can be unpacked in advance on location, for example, in a lock in front of the sterile work place and can then be brought into the sterile work place.

The particular advantage of using plastic is that it can be radiation-sterilized to a certified degree and so the required precise evidence of sterility, required particularly in biology and pharmacology, can be satisfied expediently. Here, injection-moldable plastic has the further advantage that the finished product already comes out of the injection-mold tool at a high temperature and practically germ-free.

In principle, it is of course understood that the dosing device according to the invention also allows working in classic fashion with disassembly and assembly of the add-on units. However, the particular advantage of the teaching results in complete handling of the dosing unit.

Overall, in the case of the dosing device according to the invention, as in the dosing device in the prior art, the distributor rail can also form the mechanical spine of the dosing device. However, the design is particularly expedient if the distributor rail primarily takes over the hydraulic functions of the dosing device. The distributor rail can then be detachably attached to a mechanical, elongate support structure, preferably designed as a trough or rail. Since the support structure is not exposed to the liquid to be dosed, said support structure can remain in the clean room. It can also be made from a different material than plastic. By way of example, this can be a component made of aluminum or stainless steel. It is only the distributor rail with the fluid supply line integrated therein that is replaced along with the add-on units.

Like in the prior art, it is expedient for each dosing unit to have at least one mechanical connection element for detachable mechanical attachment. In the case of a distributor rail assuming mechanical functions as well, provision can be made here for the distributor rail to have mechanical connection elements detachably engaged with the mechanical connection elements of the dosing units.

By contrast, in the case of the preferred design with a distributor rail and a mechanical support structure explained previously, provision can also be made for the mechanical support structure to have mechanical connection elements detachably engaged with the mechanical connection elements of the dosing units.

However, the design is particularly expedient if the distributor rail has mechanical connection elements detachably engaged with the mechanical connection elements of the dosing units, and if the mechanical support structure has further mechanical connection elements detachably engaged with counter elements on the distributor rail. This mechanical design, which, in a manner of speaking, is a two-stage design, results in the desired link between the distributor rail and the add-on units, which, overall, can be disposed of by replacement, while the support structure remains at the location.

There are a number of options for connecting the support structure to the distributor rail. In any case, it is recommended that the further mechanical connection elements have at least one resiliently deflectable catch.

In general, it is recommended that the mechanical connection elements are designed as latching connection elements or as bayonet-type connection elements that are opened as a result of a swivel movement or a displacing movement.

From a design point of view, it was found to be particularly expedient for the distributor rail to have a platform molded thereto, on which the dosing unit connections and, preferably, the mechanical connection elements are located. The platform at the same time stabilizes the distributor rail in its support function, and so the wall strengths can be reduced, for example in the region of the fluid supply line.

In the prior art, reference was already made to the fact that, in a dosing device of the type in question, there is usually a pressure-equalizing container, the filling volume of which is controlled to have an approximately constant value during operation, such that there is a substantially constant input pressure at the hydraulic connections of the valve units of the dosing units. This is expedient for the dosing precision of the dosing device.

It is also recommended in the case of the dosing device according to the invention that, arranged on the distributor rail, there is a pressure-equalizing container, which has a detachable hydraulic connection to the fluid supply line via a container connection. The container connection is preferably arranged between the supply connection and the first dosing unit connection. Here, it is particularly expedient if the container connection also serves for the detachable mechanical connection between the pressure-equalizing container and the distributor rail and is, for this purpose, preferably designed as a screw connection.

In principle, the fluid supply line in the distributor rail can be open at the end away from the supply connection, and so the dosing device can be installed in a liquid circuit. This may be necessary in the case of liquids to be tempered or suspensions. This can also have advantages from a cleaning point of view. However, it is particularly advantageous if the fluid supply line is closed off at the end away from the supply connection.

An overall recyclable, replaceable system is obtained using a dosing device of the type in question in which provision is furthermore made for the piston-cylinder units to be designed as replaceable parts made of preferably recyclable, preferably injection-moldable plastic and to be arranged on the valve units such that they can be mounted and dismounted in a quick, secure, impervious and detachable fashion, preferably without the need for tools, and/or for the valve units to be designed as replaceable parts made of preferably recyclable, preferably injection-moldable plastic. Individual add-on parts of the valve units, e.g. valve seats or valve springs, can possibly be made of different materials than plastic.

According to a further teaching of the invention, which is of particular importance in the case of a dosing device for liquids, comprising a distributor rail and a plurality of dosing units for the liquid that are hydraulically connected to the distributor rail, wherein each dosing unit has a valve unit, and, wherein a piston-cylinder unit is detachably arranged on each valve unit for drawing in and measured discharging of the liquid, wherein each valve unit has a hydraulic connection element for detachable hydraulic connection to the distributor rail, wherein the distributor rail has an elongate fluid supply line, at an end of which a supply connection for the liquid is provided, and which has dosing unit connections distributed laterally along its length, the dosing unit connections being detachably coupled to the hydraulic connection elements of the valve units of the dosing units, the distributor rail made of plastic and implemented according to the invention can also be further improved from a production point of view. That is, an elongate distributor rail with a multiplicity of dosing unit connections etc. requires a complex and thus expensive plastic-injection-molding tool. Here, the invention finds a remedy by virtue of the fact that the distributor rail is assembled from individual rail segments. In the process, intelligent design of the rail segments allows the rail-segment design to be largely the same and so said segments can be produced on one plastic-molding tool with replaceable mold halves. Thus, a system that can be extended in modular form is obtained, or the system of the dosing units that can be extended in modular form is now also implemented consistently in the distributor rail.

From a connection point of view, it is recommended that the rail segments are interconnected by molded-on flanges, in particular bayonet flanges, such that a practically gap-free fluid supply line is formed in the interior. A practically gap-free interior wall of the fluid supply line is of great importance in correspondingly contaminating liquids and can also reliably be achieved by a corresponding design of the rail segments.

However, the rail segment with the container connection for the pressure-equalizing container forms an exception in the design of the rail segments. Here, provision can possibly even be made for the rail segment associated with the pressure-equalizing container to be integral with the pressure-equalizing container.

What holds true overall is that the hydraulic connection elements expediently are designed as fluid-impervious plug-connection elements and/or flange-connection elements and/or have separately molded-on sealing elements or sealing elements molded on directly using the two-component injection-molding method. The same also holds true for the connections of the rail segments.

In respect of the mechanical connection elements at the various locations of the dosing device according to the invention, the use of bayonet, clamping or screw connections is recommended.

However, the subject matter of the invention is not limited to an overall dosing device for liquids, but also includes the individual components of such a dosing device as such, specifically the piston-cylinder units, the valve units, the distributor rail, the rail segments and the mechanical support structure.

In the following text, the invention will now be explained in more detail on the basis of a drawing merely illustrating preferred exemplary embodiments. In the drawing:

DETAILED DESCRIPTION OF THE INVENTION

Figure 1:
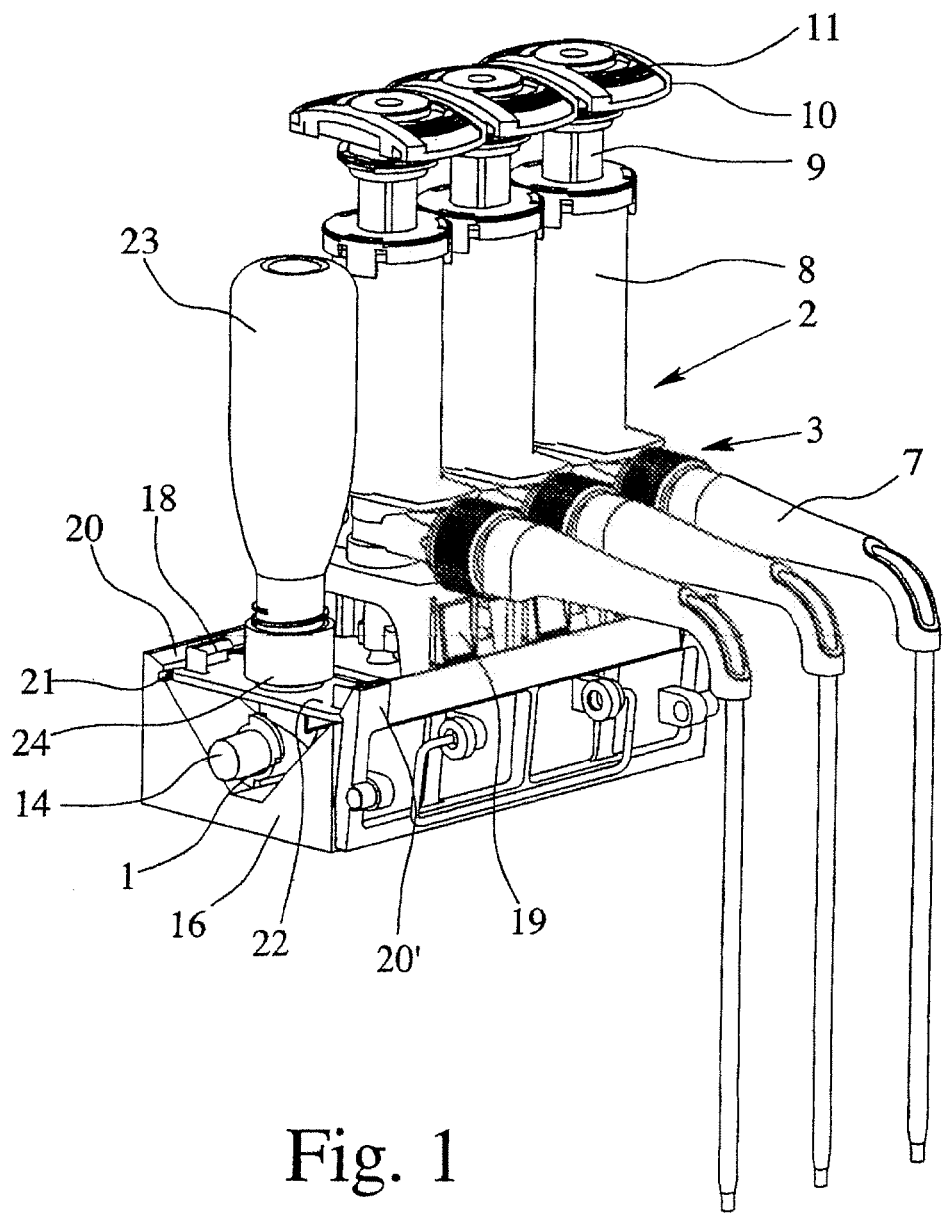
FIG. 1 is a perspective view of a first exemplary embodiment of a dosing device according to the invention for liquids in an assembled state.
Figure 6:
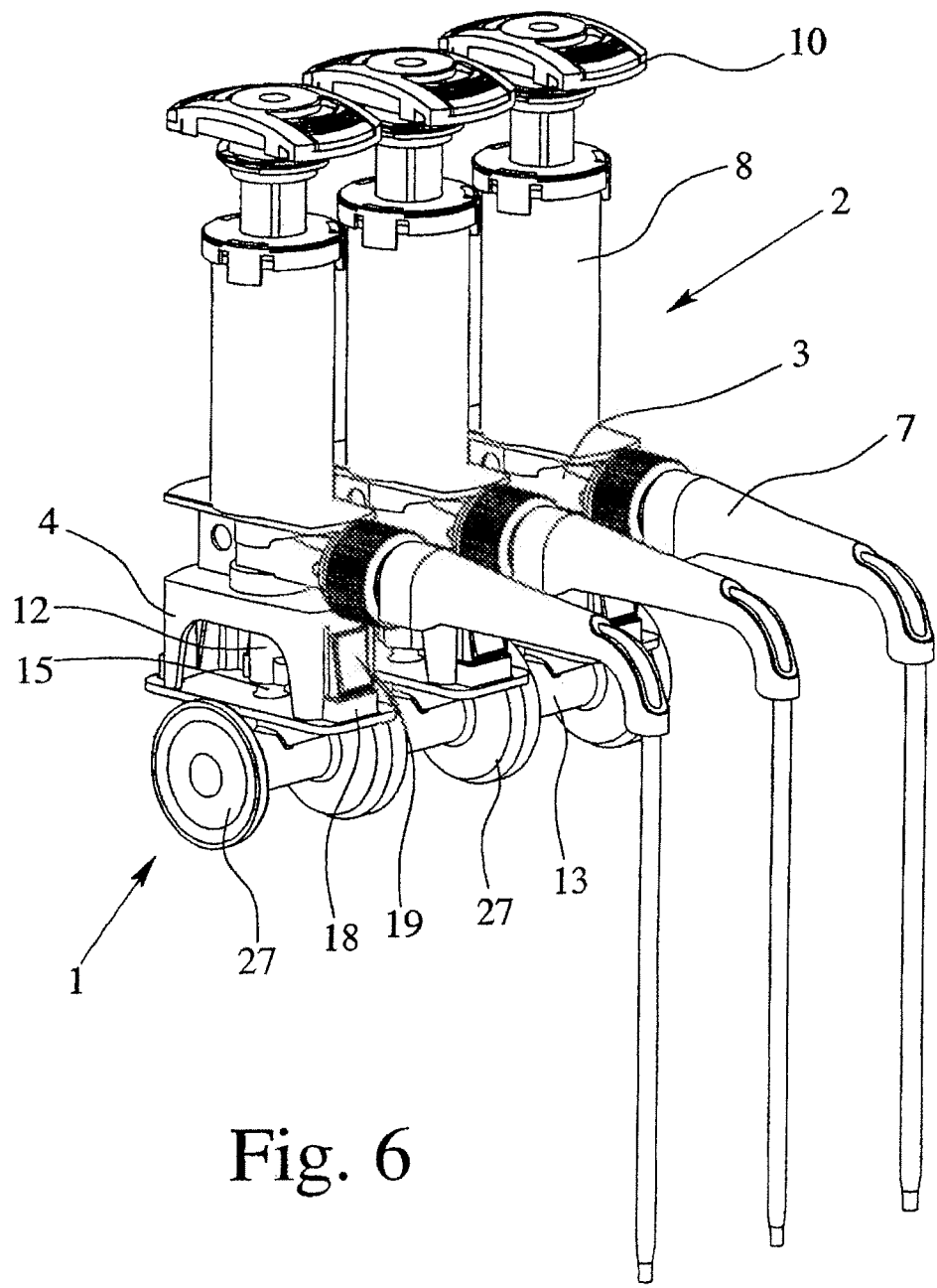
FIG. 6 is a perspective view corresponding to that of FIG. 1, showing another exemplary embodiment of a dosing device according to the invention, illustrated without a mechanical support structure.
Figure 8:
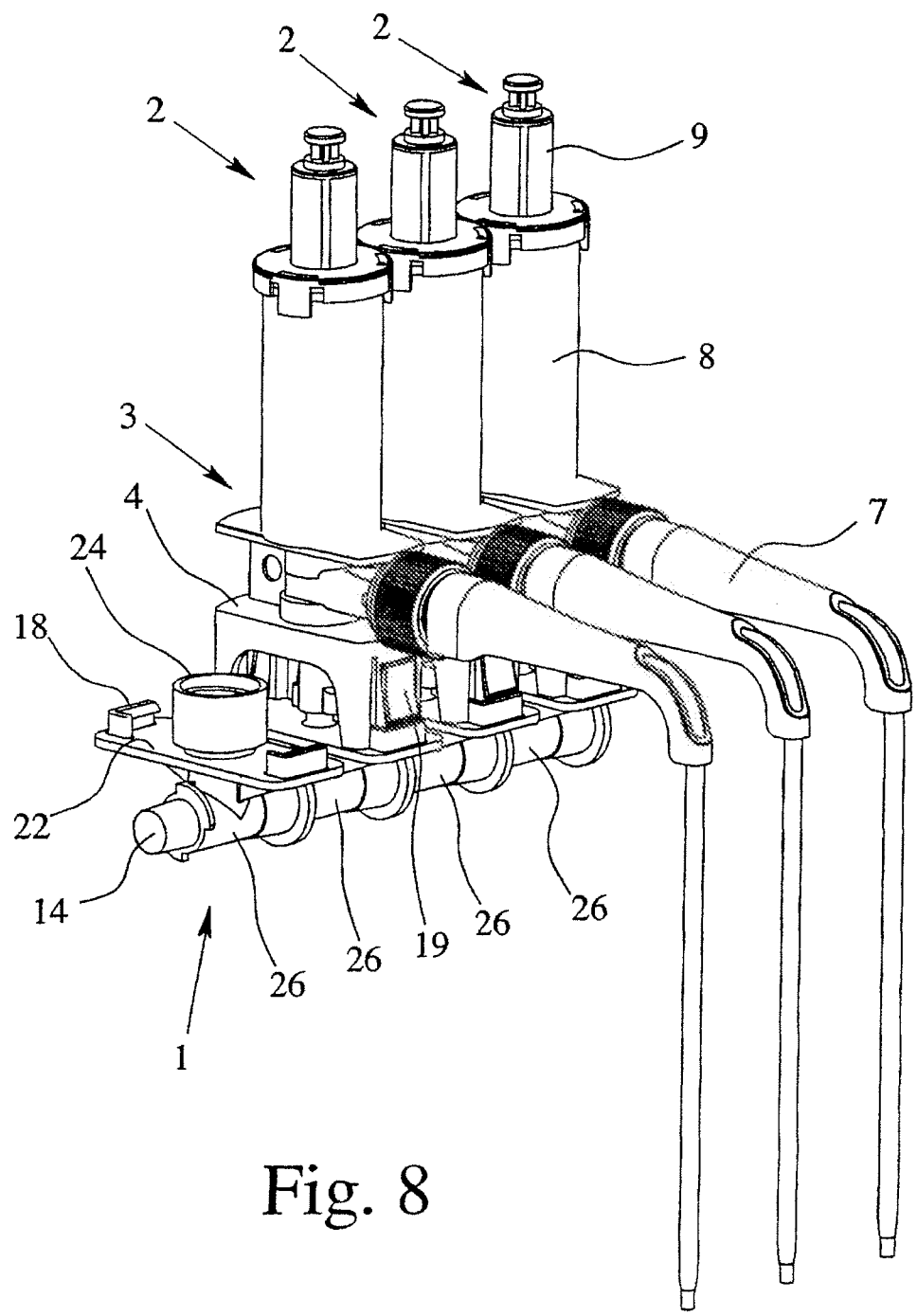
FIG. 8 is a perspective view corresponding to that of FIG. 1, but of a third exemplary embodiment of a dosing device according to the invention.

The dosing device for liquids, illustrated in three different exemplary embodiments in FIGS. 1, 6 and 8, is designed and suitable for installation in a production dosing installation. For this, reference may be made to the explanations in the introductory part of the description and the prior art cited there.

Figure 2:
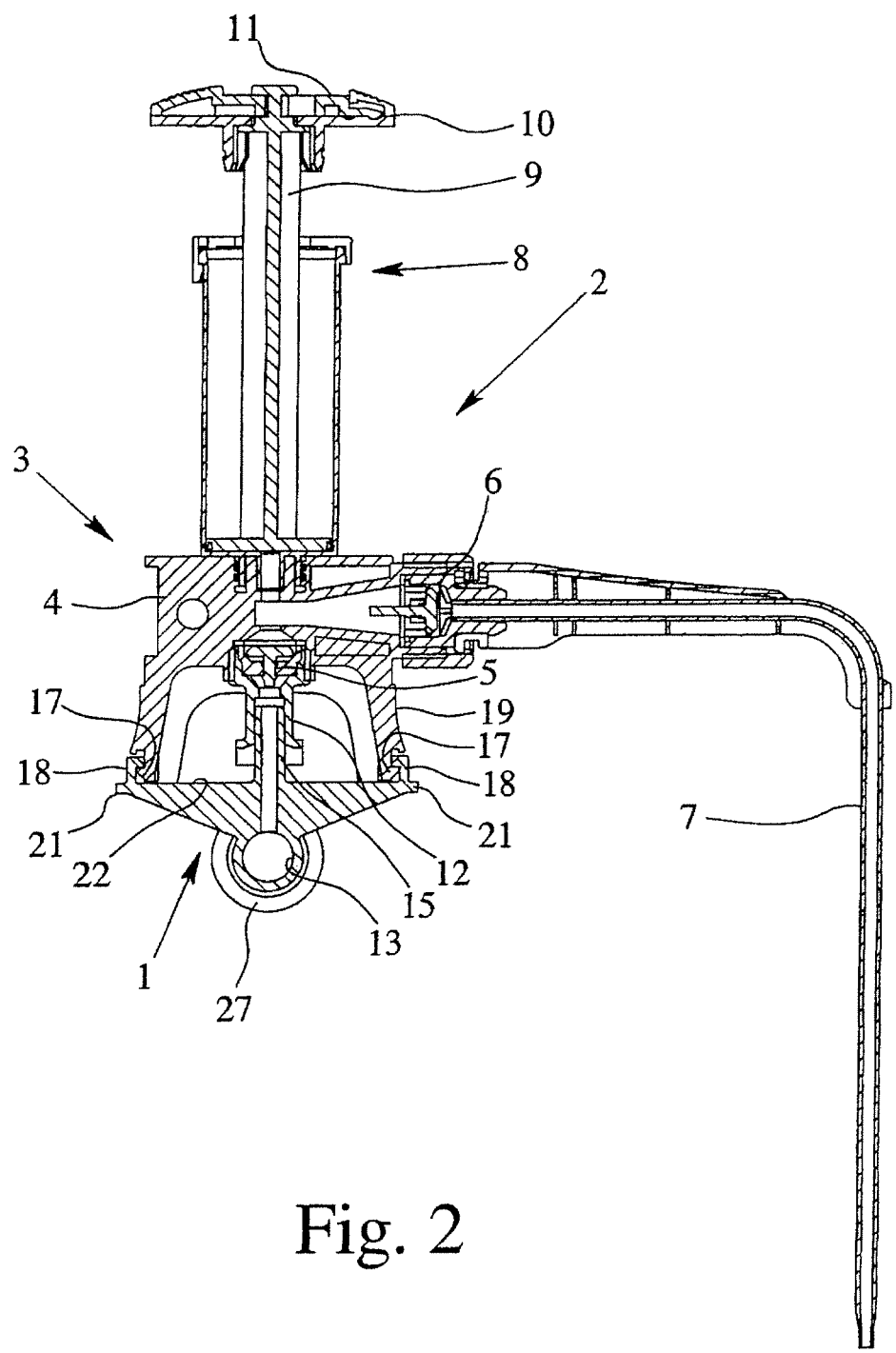
FIG. 2 shows a cross section of the dosing device of FIG. 1, but without a mechanical support structure.

The dosing device for liquids, illustrated in a perspective view in FIG. 1, firstly has a distributor rail 1 and a plurality of dosing units 2 for the liquid hydraulically connected to the distributor rail 1. Each dosing unit 2 comprises a valve unit 3, which typically and preferably has, as illustrated in FIG. 2, a valve housing 4 in which there are a suction valve 5 and a discharge valve 6, wherein a discharge cannula 7 adjoins the discharge valve 6. This is a typical valve unit of such a dosing unit, for which reference may likewise be made to the prior art.

In addition to the valve unit 3, the dosing unit 2 comprises a piston-cylinder unit 8 detachably arranged on the valve unit 3. The piston of the piston-cylinder unit 8 is attached to a piston rod 9, which projects upward and is attached to a connection head 10 at the upper end thereof. A slider 11 on the connection head 10 couples the piston rod 9 to the latter. This connection head 10 with the slider 11 is not part of the piston-cylinder unit 8, but is part of a coupling device of a motor-driven drive device (not illustrated) of the dosing installation. The exemplary embodiment illustrated in FIG. 8 shows what the ends of the piston rods 9 of the piston-cylinder units 8 look like without the connection heads 10.

Figure 3:
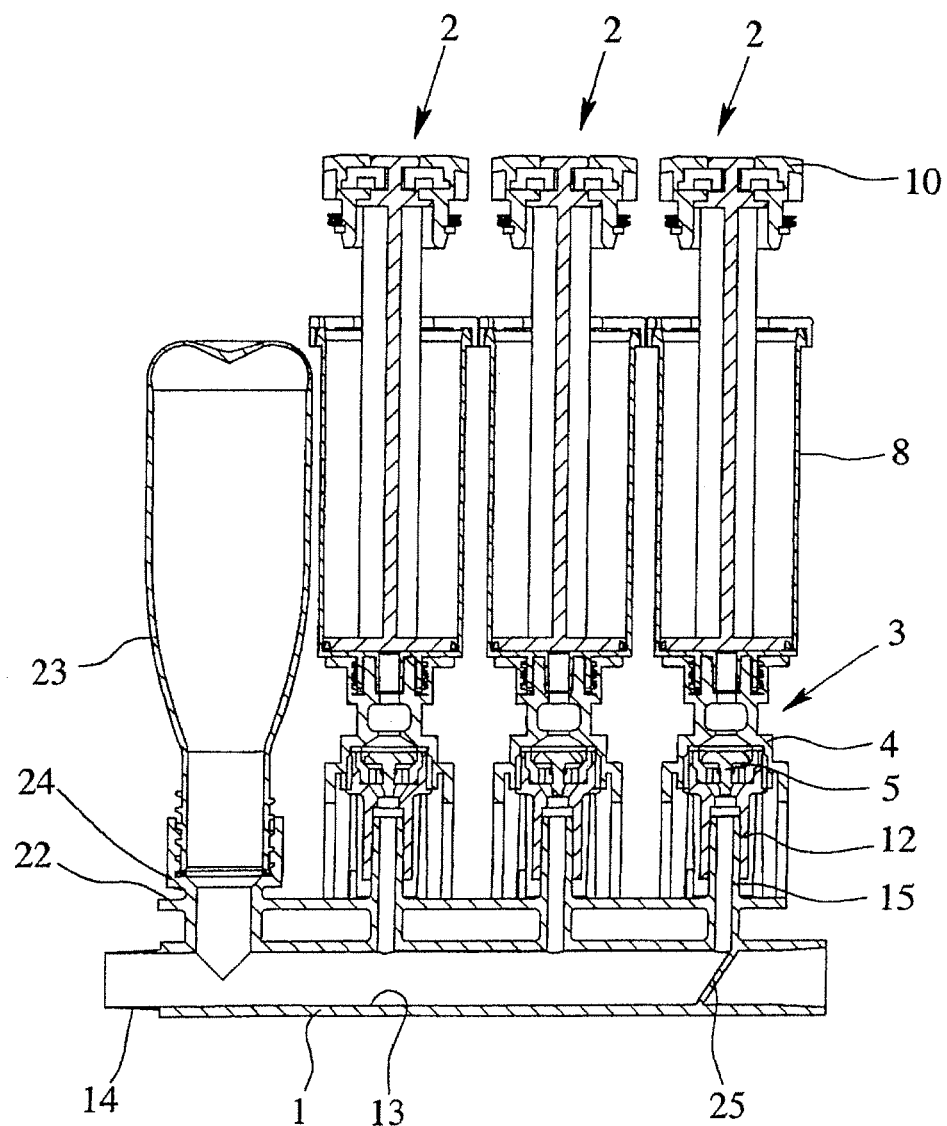
FIG. 3 is a longitudinal sectional view of the dosing device of FIG. 1, likewise, without a support structure.

FIG. 2 furthermore shows that each valve unit 3 has a hydraulic connection element 12 for detachable hydraulic connection to the distributor rail 1. The distributor rail 1 has an elongate fluid supply line 13 (FIG. 3), which has at its end side (on the left in FIGS. 1 and 3) a supply connection 14 for the liquid and has a plurality of dosing unit connections 15 distributed laterally along its length and preferably arranged with equidistant spacing. FIG. 3 shows the dosing unit connections 15 projecting upward from the fluid supply line 13. In FIG. 2, the dosing unit connection 15 engages with the hydraulic connection element 12 in an impervious fashion. Thus, the dosing unit connections 15 are coupled to the hydraulic connection elements 12 in a hydraulically sealed and mechanically detachable fashion.

Now, it is essential for the teaching of the invention that, firstly, the distributor rail 3 is designed as a replaceable part made of a preferably recyclable, preferably injection-moldable plastic. The components of the valve unit 3 and of the piston-cylinder unit 8 are also parts made of plastic, preferably of recyclable and preferably also injection-moldable plastic.

FIG. 1 shows a particular design of the dosing device according to the invention, which is distinguished by virtue of the fact that the distributor rail 1 is detachably attached to a mechanical, elongate support structure 16, preferably designed as a trough or rail. Here, the illustrated and preferred exemplary embodiment provides for the mechanical support structure 16 to be designed as a component made of metal or plastic that is not designed to be discarded. In particular, the support structure 16 can be a component made of aluminum or stainless steel. The additional mechanical support structure 16, which does not contact the liquid to be dosed anywhere, can remain in the clean room, i.e., it does not have to be replaced. Only the components contacting the liquid are replaced, to be precise in the fashion according to the invention that is particularly expedient in respect of the requirements of the pharmaceutical industry.

FIGS. 1 and 2 show that, in the illustrated and in this respect preferred exemplary embodiment, each valve unit 3 has at least one mechanical connection element 17 for detachable mechanical attachment of the dosing unit 2. FIG. 2 furthermore shows that, in the illustrated exemplary embodiment, the distributor rail 1 has mechanical connection elements 18, which detachably engage with the mechanical connection elements 17 of the dosing units 2 in an interlocking fashion. FIG. 2 shows that the connection elements 17, 18 are designed as hook-shaped elements that can be made to engage with one another.

FIGS. 1, 2 and 6, in particular, clearly show that the connection elements 17 of the valve units 3, which elements implement the detachable engagement, are designed in an elastically resilient fashion and can be pressed back by pressure on a finger pushbutton 19 and can be lifted out of the opposing connection elements 18.

Figure 5:
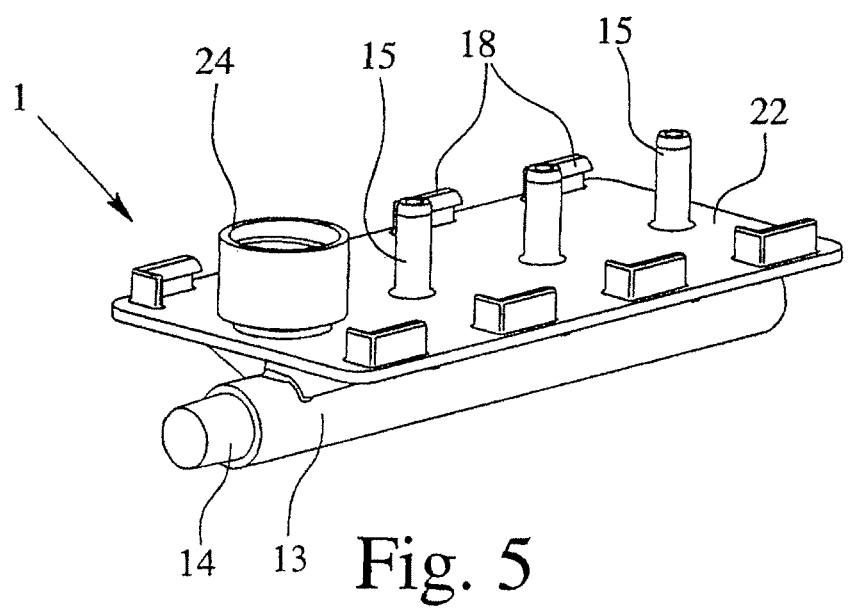
FIG. 5 is a perspective view of the distributor rail.

FIG. 5 shows how the connection elements 18 can be expediently arranged on the distributor rail 1, such that there is anti-twist protection for the valve unit 3 on the distributor rail 1. All these design features have already been implemented in the dosing device known from the prior art and so reference may be made to the prior art cited at the outset.

In principle, it would be possible for the mechanical support structure to have mechanical connection elements that detachably engage with the mechanical connection elements of the dosing units, the latter elements preferably being arranged on the valve units. However, this is not illustrated in the drawings. Rather, what is illustrated there is that the mechanical support structure 16 has further mechanical connection elements 20, which are detachably engaged with counter elements 21 on the distributor rail 1. This can be seen in FIG. 1 and the counter elements 21 are shown as edges of the distributor rail 1 in FIG. 2. Here, FIG. 1 shows a special design measure to the extent that, on the right-hand side, a resilient catch 20' forms one of the opposing mechanical connection elements 20. This resilient catch 20' as a connection element securely fastens the distributor rail 1 to the mechanical support structure 16.

Figure 11:
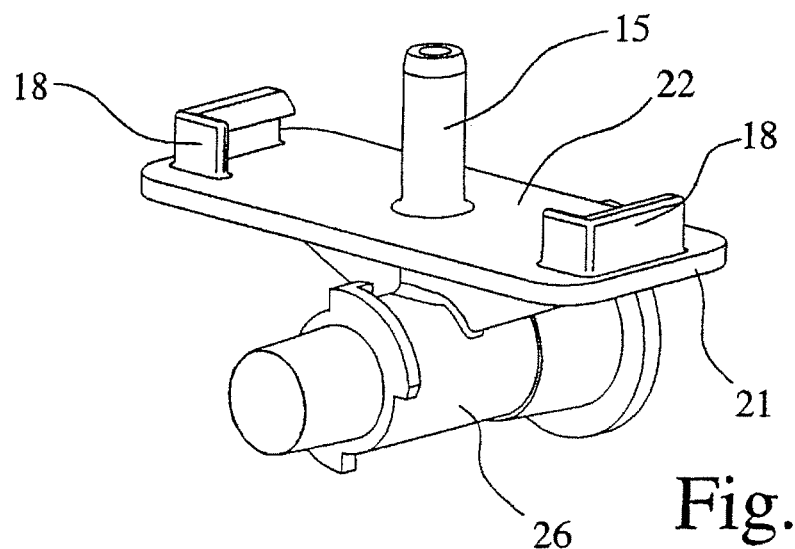
FIG. 11 is a perspective view of the rail segment shown in FIG. 10.

The exemplary embodiments illustrated in the drawing correspond in that the respectively illustrated distributor rail 1 also has the mechanical connection elements 18 to the valve units 3. For this, provision is regularly made for the distributor rail 1 to have a molded-on platform 22 on which the dosing unit connections 15 and, in this case too, the mechanical connection elements 18 are located. This can be seen particularly well in FIGS. 2 and 5, and, correspondingly, in FIGS. 11 and 13.

FIG. 2 shows the distributor rail 1 as a component produced entirely from plastic and preferably produced using the injection-molding method, on which are formed the upwardly projecting dosing unit connection 15 on the platform 22 and, laterally, the hook-shaped mechanical connection elements 18 and the counter elements 21 protruding from the edge for attachment to the mechanical support structure 16. The connection elements 17, 18 on the one hand, and the connection elements 20 with the counter elements 21 on the other hand are in this case designed as interlocking bayonet connections. Alternatively, they can be designed as screw connections or force-fit clamping connections (not illustrated here). The fluid supply line 13 running in the longitudinal direction can be seen at the bottom of FIG. 2.

Figure 4:
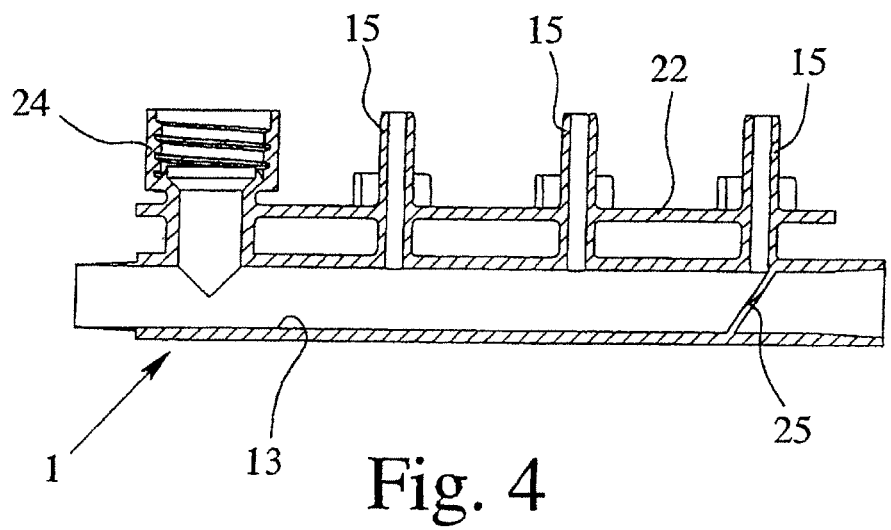
FIG. 4 is a longitudinal sectional view of a distributor rail of the dosing device shown in FIG. 1.

Common to the exemplary embodiments of FIGS. 1, 3, 5 and FIGS. 8, 9 is that, arranged on the distributor rail 1, there is a pressure-equalizing container 23, which has a detachable hydraulic connection to the fluid supply line 13 via a container connection 24. The container connection 24 preferably is arranged between the supply connection 14 and the first dosing unit connection 15. In the illustrated and in this respect preferred exemplary embodiment, provision is made in this case for the container connection 24 also to serve for the detachable mechanical connection between the pressure-equalizing container 23 and the distributor rail 1. For this, it is designed as a screw connection (FIG. 4) in this case.

As already mentioned initially, it is in principle possible for the fluid supply line 13 to be open at the end away from the supply connection 14 and to be provided with a corresponding connection. Then the dosing device overall can be installed in a circulating system. However, all of the exemplary embodiments illustrated here show an embodiment in which the fluid supply line 13 is closed off at the end away from the supply connection 14. Here, FIG. 3 shows that the closing-off has been implemented by an impact surface 25 arranged obliquely in the fluid supply line 13, and so this results in a clearance-volume-free deflection of the liquid flow upward into the dosing unit connection 15 at the right-hand end of the fluid supply line 13. This is also a feature for the relevant intended use according to the invention.

It was already mentioned at the outset that the basic goal of the dosing device according to the invention for liquids was the implementation of complete replaceability of the parts of the dosing device. According to a preferred teaching of the invention, this is achieved by virtue of the fact that the piston-cylinder units 8 are designed as replaceable parts made of preferably recyclable, preferably injection-moldable plastic and are arranged on the valve units 3 such that they can be mounted and dismounted in a quick, secure, impervious and detachable fashion, preferably without the need for tools, and the valve units 3 are designed as replaceable parts made of preferably recyclable, preferably injection-moldable plastic, wherein individual add-on parts of the valve units 3 can possibly be made of different materials than plastic.

The exemplary embodiment in FIGS. 1-5 shows a coherent, integral distributor rail 1 made of recyclable, injection-moldable plastic. However, this is a comparatively expensive conceptual design because the tool required for this is large, complicated and individual for the number of connections.

By contrast, the exemplary embodiments in FIGS. 6-7 and FIGS. 8-13 show a segmented, i.e., modularly assembled, distributor rail 1. Here, provision is made for the distributor rail 1 to be assembled from individual rail segments 26. Thus, a dosing device can have virtually any length, i.e., in principle, any number of rail segments 26 can be interconnected in a modular fashion in order to be able to take into consideration a correspondingly large number of dosing units 2.

In principle, in later stages of production, the separately produced rail segments 26 can be connected to form a permanently undetachable, complete distributor rail 1 using permanent connection techniques, such as soldering, welding or adhesive bonding.

Figure 7:
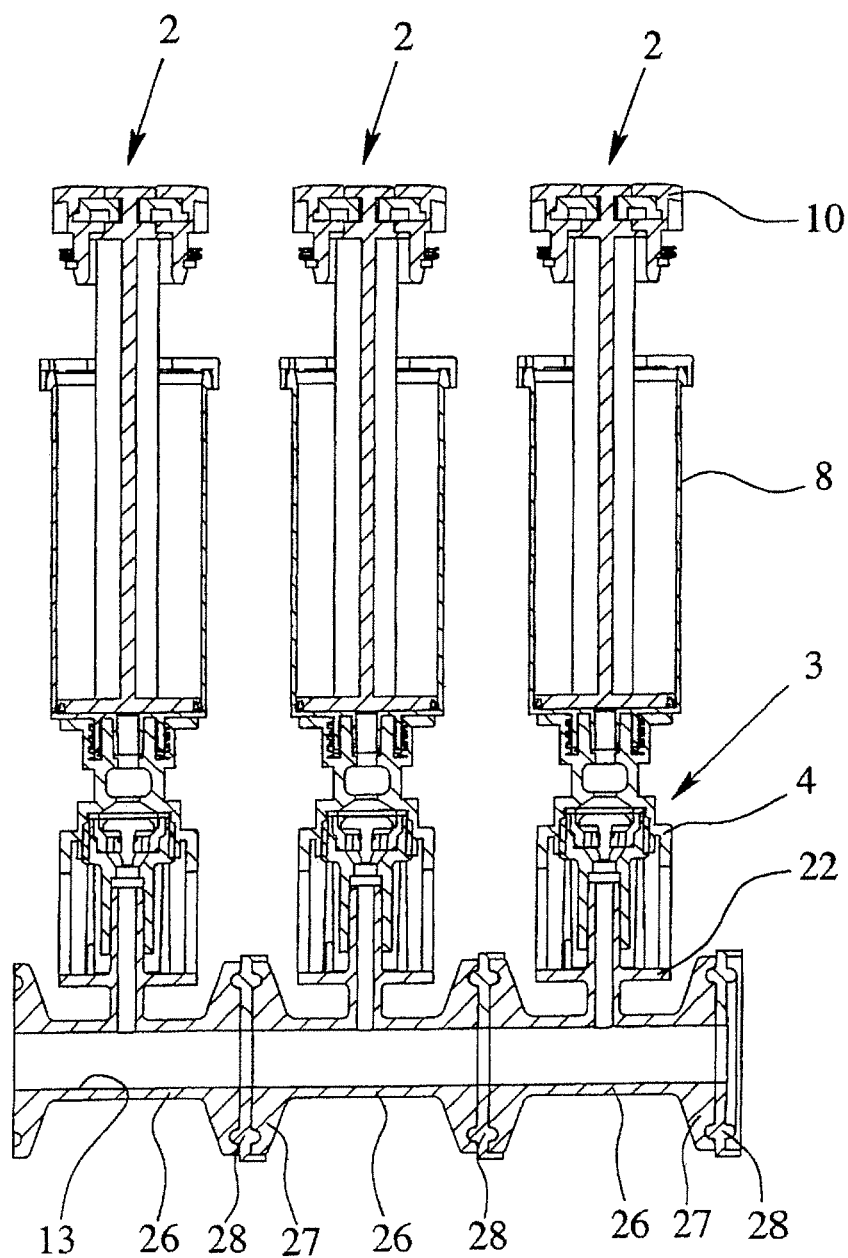
FIG. 7 shows a cross section corresponding to that in FIG. 3, but of the dosing device of FIG. 6.

The exemplary embodiment illustrated in FIGS. 6 and 7 shows a design in which the rail segments 26 are interconnected by molded-on plate-shaped flanges 27 in such a way that a practically gap-free fluid supply line 13 is formed in the interior. In the exemplary embodiment illustrated here, this is achieved by (see, in particular, FIG. 7) chemical-resistant sealing disks 28 being located between the flanges 27, these disks being precisely formed and positioned. The flanges 27 can be braced by force acting axially with respect to the fluid supply line 13 as a result of clamps applied to the outside. This is a conventional attachment technique.

For the distributor rail 1, use can be made of, for example, polypropylene, strengthened polypropylene or, in special cases, PEEK (Polyether ether ketone) as well. Examples of the materials for the sealing disks 28 are silicone-based sealing plastics or EPDM (ethylene propylene diene monomer).

The sealing disks 28 can also be molded onto one of the two involved flanges 27. FIG. 7 shows this at the end on the right. For this, a two-component injection-molding method is suitable.

In the exemplary embodiment illustrated in FIG. 8 ff., the gap-free design of the fluid supply line 13 has been implemented by a corresponding design of the rail segments 26, which can be inserted into one another. This can be seen particularly well in the section in FIG. 10. In FIG. 10, the wall of the rail segment 26 terminates toward the left in a thin-walled end, and so it is possible to insert the two walls of adjacent rail segments 26 due to the corresponding conical bevel (on the right in FIG. 10). Here, adjacent rail segments 26 are connected without seals by means of flanges 27 designed as bayonet flanges, and so external clamps or the like are not required. This can be seen particularly well in FIG. 9.

Overall, what can be gathered from the illustrations of the exemplary embodiments explained now is that the rail segments 26 largely have the same design, such that they can be produced on one plastic-molding tool, possibly only with adapted sliders. By way of example, it can be seen in FIG. 10 that the final segment of the distributor rail 1 lying on the right-hand side shows that in this case the already mentioned impact surface 25 is formed in the interior of the fluid supply line 13 by the use of corresponding sliders. The bayonet flange 27 is unnecessarily molded thereon on the right, but this is precisely due to the use of the same tool as for the normal rail segments 26.

Figure 12:
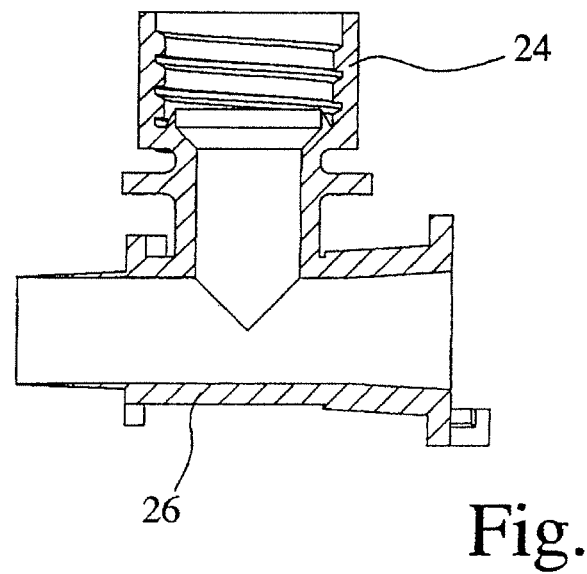
FIG. 12 shows a rail segment with a container connection in an illustration corresponding to FIG. 10.
Figure 13:
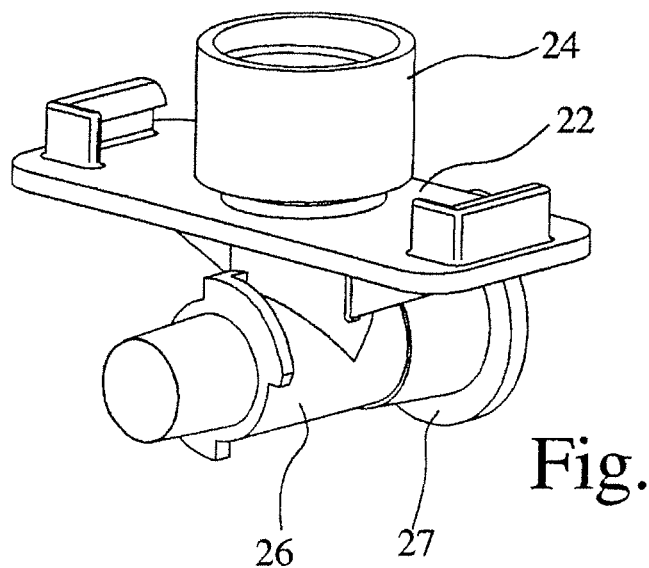
FIG. 13 is a perspective view of the rail segment of FIG. 12.

It can also be seen in the illustration in FIGS. 12 and 13 that changes on the tool in the upper region were necessary here as a result of forming the container connection 24. However, the conventional tools were, moreover, used, and so, here too, the platform 22 is implemented with the hook-shaped connection elements 18.

Figure 9:
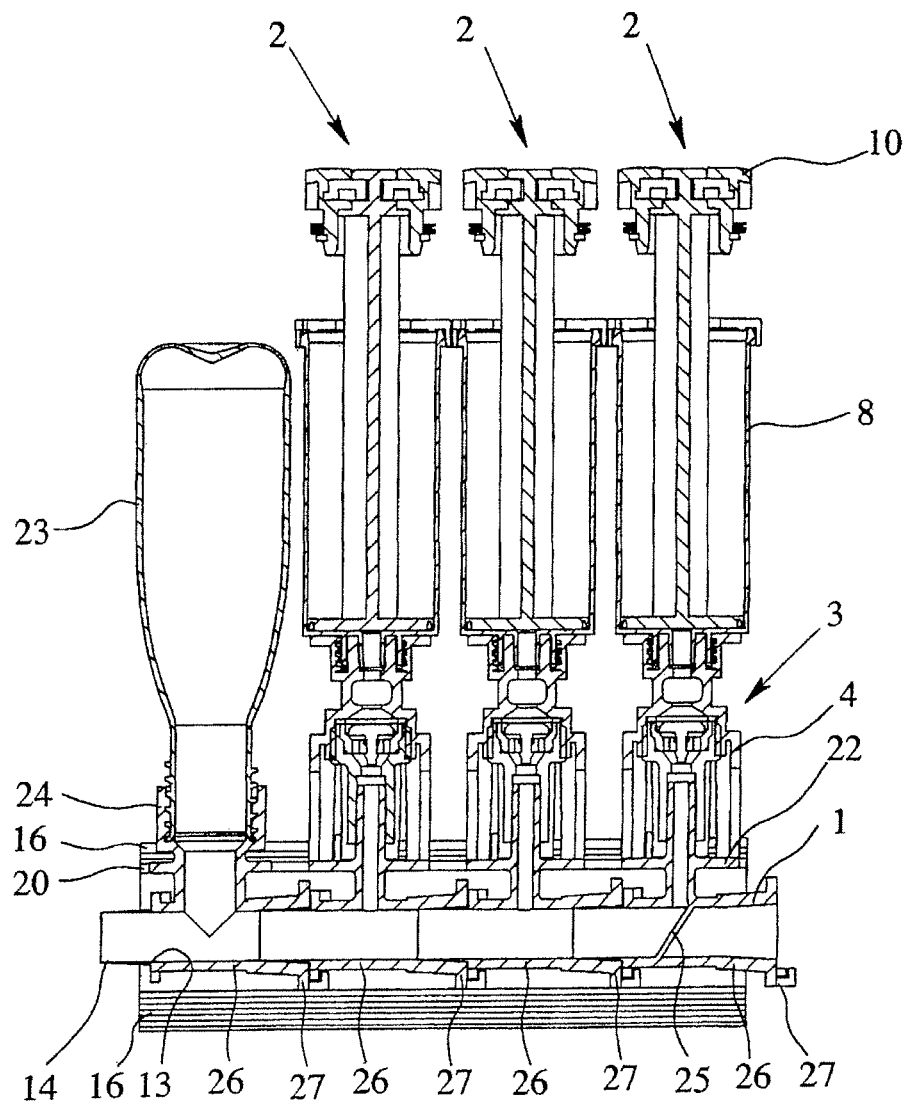
FIG. 9 shows a cross section corresponding to that of FIG. 3, but of the dosing device of FIG. 8, this time with a mechanical support structure.
Figure 10:
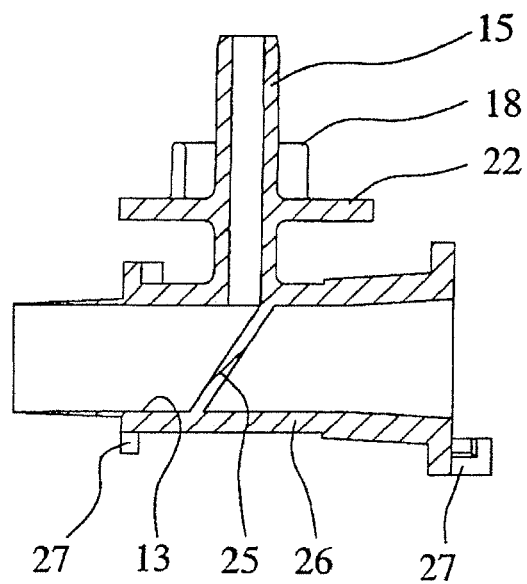
FIG. 10 is a longitudinal sectional view of a rail segment of the distributor rail of the exemplary embodiment of FIG. 8, in this case, of a last, closed rail segment.

The illustrated exemplary embodiment moreover shows the container connection 24 as a screw connection for the pressure-equalizing container 23 that is made of plastic and can be seen, for example, in FIG. 9. Other connection techniques, i.e. interlocking or friction-fit variants, are possible.

A variant in which the pressure-equalizing container 23 is integrally molded on the corresponding rail segment 26 is not illustrated.

The dosing device illustrated in FIG. 8 is the replacement part, as can be packaged and provided in a sterile state. This component can also comprise a pressure-equalizing container 23 in addition to the illustrated piston-cylinder units 2, the valve units 3 and the distributor rail 1. This complete replacement part is only hydraulically coupled to the supply connection 14. Even the latter place of potential contamination could be eliminated by a lengthened supply connection as an integral or preassembled sterilized line connected outside of the clean room. From a mechanical point of view, the replacement part is connected to the coupling device of the motor-driven drive device of the dosing installation at the end of the piston rods 9 of the cylinder-piston arrangements 2. Moreover, it is mechanically connected to the platform 22 with the support structure 16.

In the illustration of FIG. 9, the exemplary embodiment illustrated there allows identification of the existence of the mechanical support structure 16. Here, overall, it is again possible to resort to FIG. 1. Even in the segmented refinements of the distributor rail 1 realized in the explained exemplary embodiments, the individual rail segments 26 have corresponding platforms 22, i.e., in principle, the section thereof appears as in the illustration of FIG. 2.

Now, the platforms 22 could be inserted one after the other into corresponding rails of the support structure 16 in the longitudinal direction. These rails would then form the mechanical connection elements 20 at the support structure 16. This could be brought about in the longitudinal direction, but corresponding rails in each case could be arranged in the transverse direction, respectively forming individual compartments. However, attaching the rail segments 26 to the mechanical support structure 16 is simpler using the snap-on design shown in FIG. 1.

In principle, a further variant of the mechanical connection technique can be implemented, which is not illustrated in the drawing. In this bayonet-like connection technique, a displacement movement running in the plane of the platform is realized, which results in locking or unlocking.

What is claimed is:

1. A dosing device for liquids, comprising:
   a distributor rail comprising an elongate fluid supply line,
   a plurality of dosing units for a liquid that are hydraulically connected to the fluid supply line of the distributor rail,
   wherein each dosing unit has a valve unit, and a piston-cylinder unit for drawing in and measured discharging of the liquid that is detachably arranged on the valve unit,
   wherein each valve unit has a hydraulic connection element for detachable hydraulic connection to the fluid supply line of the distributor rail,
   wherein the fluid supply line has dosing unit connections distributed laterally along its length, the dosing unit connections being detachably coupled to the hydraulic connection elements of the valve units of the dosing units,
   wherein at the end of the fluid supply line, a supply connection for the liquid is provided,
   wherein the distributor rail is a replaceable part made of a plastic,
   wherein the distributor rail is detachably attached to an elongate mechanical support structure, and
   wherein the mechanical support structure has further mechanical connection elements which detachably engage counter elements on the distributor rail securely fastening the distributor rail to the mechanical support structure.

2. The dosing device as claimed in claim 1, wherein the dosing unit connections of the distributor rail are arranged with equidistant spacing.

3. The dosing device as claimed in claim 1, wherein the distributor rail is made of a recyclable, injection-moldable plastic.

4. The dosing device as claimed in claim 1, wherein each dosing unit has at least one mechanical connection element for detachable mechanical attachment to the distributor rail or to the support structure.

5. The dosing device as claimed in claim 4, wherein the mechanical support structure has mechanical connection elements detachably engaged with the mechanical connection elements of the dosing units.

6. The dosing device as claimed in claim 4, wherein the distributor rail has mechanical connection elements detachably engaged with the mechanical connection elements of the dosing units.

7. The dosing device as claimed in claim 6, wherein the distributor rail has a platform molded thereto, and wherein the dosing unit connections and the mechanical connection elements are located on the platform.

8. The dosing device as claimed in claim 1, wherein the further mechanical connection elements have at least one resiliently deflectable catch.

9. The dosing device as claimed in claim 1, wherein a pressure-equalizing container is arranged on the distributor rail, the pressure-equalizing container being detachably hydraulically connected to the fluid supply line via a container connection.

10. The dosing device as claimed in claim 9, wherein the container connection also provides a detachable screw connection between the pressure-equalizing container and the distributor rail.

11. The dosing device as claimed in claim 1, wherein the fluid supply line is closed off at a distal end relative to the supply connection.

12. The dosing device as claimed in claim 1, wherein the distributor rail is formed of a plurality of individual rail segments connected by means of respective connection elements.

13. The dosing device as claimed in claim 12, wherein the connection elements of the rail segments are molded-on flanges such that a practically gap-free fluid supply line is formed in the interior of the supply line.

14. The dosing device as claimed in claim 12, wherein the rail segments are essentially identical.

15. The dosing device as claimed in claim 12, wherein the connection elements of the rail segments are fluid-impervious plug-connections or flange-connection elements.

16. The dosing device as claimed in claim 12, wherein the connection elements of the rail segments have molded-on sealing elements.

17. The dosing device as claimed in claim 1, wherein the piston-cylinder units are replaceable parts made of plastic and are arranged on the valve units such that they can be mounted and dismounted in a secure, impervious and detachable fashion.

18. The dosing device as claimed in claim 17, wherein the piston-cylinder units are arranged on the valve units in a manner enabling mounting and dismounting thereof without tools.

19. The dosing device as claimed in claim 17, wherein the valve units are replaceable parts made of plastic.

20. The dosing device as claimed in claim 1, wherein the distributor rail is made of a recyclable, injection-moldable plastic, wherein each dosing unit has at least one mechanical connection element for detachable mechanical attachment to the distributor rail and the distributor rail has mechanical connection elements detachably engaged with the connection elements of the dosing units, wherein the distributor rail is formed of individual rail segments connected by means of respective connection elements, wherein at least one of the hydraulic connection elements and the connection elements of the rail segments comprise at least one of fluid-impervious plug-connection elements and flange-connection elements, and wherein the piston-cylinder units are replaceable parts made of plastic and are arranged on the valve units in a manner enabling mounting and dismounting in a secure, impervious and detachable fashion.

21. The dosing device as claimed in claim 20, wherein the distributor rail has a platform molded thereto, wherein the dosing unit connections and the mechanical connection elements are located on the platform, and wherein the rail segments are interconnected by molded-on flanges such that an essentially gap-free fluid supply line is formed in the interior of the supply line.

22. A dosing device for liquids, comprising:
a distributor rail comprising an elongate fluid supply line, and
a plurality of dosing units for the liquid that are hydraulically connected to the fluid supply line of the distributor rail,
wherein each dosing unit has a valve unit, and,
wherein a piston-cylinder unit is detachably arranged on each valve unit for drawing in and measured discharging of the liquid,
wherein each valve unit has a hydraulic connection element for detachable hydraulic connection to the fluid supply line of the distributor rail,
wherein the fluid supply line has dosing unit connections distributed laterally along its length, the dosing unit connections being detachably coupled to the hydraulic connection elements of the valve units of the dosing units,
wherein at an end of the fluid supply line, a supply connection for the liquid is provided
wherein the distributor rail is a replaceable part made of a plurality of individual plastic rail segments that are connected by means of respective connection elements.

23. The dosing device as claimed in claim 22, wherein the connection elements of the rail segments are molded-on flanges in a manner producing an essentially gap-free fluid supply line.

24. The dosing device as claimed in claim 22, wherein the rail segments are essentially identical.

25. The dosing device as claimed in claim 22, wherein the connection elements of the rail segments are at least one of fluid-impervious plug-connection elements and flange-connection elements.

26. The dosing device as claimed in claim 22, wherein the rail segments are connected by molded-on sealing elements.

27. The dosing device as claimed in claim 22, wherein the piston-cylinder units are replaceable parts made of plastic and are arranged on the valve units enabling mounting and dismounting thereof in a secure, impervious and detachable fashion.

28. The dosing device as claimed in claim 27, wherein the valve units are replaceable parts made of plastic.

29. The dosing device as claimed in claim 22, wherein the distributor rail is detachably attached to a elongate, mechanical support structure.

30. The dosing device as claimed in claim 22, wherein the distributor rail has a platform molded thereto, on which the dosing unit connections and the mechanical connection elements detachably engaged with mechanical connection elements of the dosing units are located.

31. The dosing device as claimed in claim 22, wherein a pressure-equalizing container is arranged on the distributor rail, the pressure-equalizing container being detachably hydraulically connected to the fluid supply line via a container connection.

32. The dosing device as claimed in claim 31, wherein the container connection also provides a detachable screw connection between the pressure-equalizing container and the distributor rail.

33. The dosing device as claimed in claim 22, wherein the fluid supply line is closed off at distal end relative to the supply connection.

* * * * *